United States Patent
Rothenberg

(10) Patent No.: US 10,307,093 B2
(45) Date of Patent: Jun. 4, 2019

(54) PLACENTAL AND CORD BLOOD COLLECTION DEVICE WITH SAFETY

(71) Applicant: Becton, Dickinson and Company, Franklin Lakes, NJ (US)

(72) Inventor: Ashley Rachel Rothenberg, Morris Plains, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 205 days.

(21) Appl. No.: 14/204,032

(22) Filed: Mar. 11, 2014

(65) Prior Publication Data

US 2014/0276219 A1 Sep. 18, 2014

Related U.S. Application Data

(60) Provisional application No. 61/787,396, filed on Mar. 15, 2013.

(51) Int. Cl.
*A61B 5/15* (2006.01)
*A61B 5/153* (2006.01)

(52) U.S. Cl.
CPC ........ *A61B 5/150068* (2013.01); *A61B 5/153* (2013.01); *A61B 5/150038* (2013.01); *A61B 5/150045* (2013.01); *A61B 5/150748* (2013.01); *A61B 5/150259* (2013.01); *A61B 5/150633* (2013.01); *A61B 5/150885* (2013.01)

(58) Field of Classification Search
CPC ..... A61B 5/15; A61B 5/150068; A61B 5/153; A61B 5/150038; A61B 5/150045
See application file for complete search history.

(56) References Cited

U.S. PATENT DOCUMENTS

| | | | |
|---|---|---|---|
| 5,009,657 A * | 4/1991 | Cotey | A61B 17/122 606/120 |
| 5,372,581 A | 12/1994 | Anderson | |
| 5,575,795 A | 11/1996 | Anderson | |
| 5,575,796 A | 11/1996 | King et al. | |
| 5,690,646 A | 11/1997 | Gruenberg | |
| 6,254,575 B1 * | 7/2001 | Thorne, Jr. | A61M 5/1782 128/919 |
| 8,216,249 B2 | 7/2012 | Watson et al. | |
| 2004/0172043 A1 * | 9/2004 | Watson, Jr. | A61B 17/128 606/120 |
| 2005/0054982 A1 | 3/2005 | Bellucci et al. | |
| 2005/0197596 A1 | 9/2005 | Bellucci et al. | |

(Continued)

FOREIGN PATENT DOCUMENTS

| | | |
|---|---|---|
| DE | 10-2009-047666 | 6/2011 |
| FR | 2954085 | 6/2011 |
| WO | WO-01/76660 | 10/2001 |

(Continued)

OTHER PUBLICATIONS

English Translation of DE 10 2009047666.*

(Continued)

*Primary Examiner* — Daniel L Cerioni
*Assistant Examiner* — Yasmeen S Warsi
(74) *Attorney, Agent, or Firm* — Servilla Whitney LLC

(57) ABSTRACT

A novel blood collection device is described to secure a needle in place in a placenta or umbilical cord to prevent needle stick before, during, and after cord blood collection procedure.

18 Claims, 2 Drawing Sheets

(56) References Cited

U.S. PATENT DOCUMENTS

2008/0228153 A1     9/2008  Shacham
2012/0232356 A1*    9/2012  Coelho ................ A61B 5/0205
                                                        600/301

FOREIGN PATENT DOCUMENTS

WO    WO-2004/043225    5/2004
WO    WO-2011/093781    8/2011

OTHER PUBLICATIONS

PCT International Preliminary Report on Patentability in PCT/US2014/027620, dated Sep. 24, 2015, 7 pages.
PCT International Search Report and Written Opinion in PCT/US2014/027620, dated Jun. 3, 2014, 10 pages.

* cited by examiner

PLACENTAL AND CORD BLOOD COLLECTION DEVICE WITH SAFETY

CROSS-REFERENCE TO RELATED APPLICATIONS

This application claims priority under 35 U.S.C. § 119(e) to U.S. Provisional Application No. 61/787,396, filed Mar. 15, 2013, the disclosures of which are incorporated herein by reference in their entirety.

TECHNICAL FIELD

An aspect of the present invention relates generally to a blood collection device to secure a needle in place in an umbilical cord or placenta in a safe and secure manner. The blood collection device prevents needle stick injuries from occurring before, during, and after a cord blood collection procedure. Aspects of the present invention also relate to a blood collection device that include a retractable needle and reuse prevention features and methods of using such needle assemblies.

BACKGROUND

Placental and umbilical cord blood collection procedures currently utilize a 17 gauge needle attached to a collection bag. The placental and cord blood collection procedure is currently performed by a health care provider using hands to stabilize the needle and the placenta or umbilical cord because no other technique or methods have been successful. The current procedure poses a hazard of possible needle stick to the health care provider during insertion of the needle into the slippery cord.

Currently known devices include a two part collection container in which a portion of the umbilical cord is cut and placed within the container. The umbilical cord is then allowed to drip or empty its blood content into the collection container. Since the collection method is via a drip, there is also potential for contamination of the blood sample with the mother's blood. The device is primarily aimed at collection of blood from the umbilical cord in small amounts for testing as it does not collect blood via needle insertion into the umbilical vein.

Other safety devices employ safety features only during needle insertion and do not protect the user from needle stick injuries before and after use of the needle.

One device provides a needle impenetrable device to receive the cord and secure it in place during insertion. However, the device includes a needle on a "malleable arm" and does not include needle protection before insertion e.g. a retractable needle or following insertion and completion of collection. There is therefore still an opportunity for needle stick injury to the user after needle is removed from umbilical cord.

Therefore there is a need for a placental and cord blood collection device that secures a needle in place in an umbilical cord and provides safety during the entire collection process by having the needle protected before, during, and after use, to help solve the safety problem currently encountered during cord blood collection. The present invention solves the need by providing a blood collection safety device to prevent needle stick before, during, and after use, while also reducing the risk of contamination with the mother's blood during cord blood collection.

SUMMARY

One aspect of the present invention pertains to a blood collection device comprising a housing to secure an umbilical cord having a first curved sidewall with a first finger hold and a second curved sidewall with a second finger hold; a hinging member for pivotally securing said first sidewall to said second sidewall; and a needle access point disposed in the housing for needle insertion.

In one or more embodiments, the device may further comprise a needle safety element comprises a retractable needle disposed in a chamber that may be integrally connected to the needle access point. In one or more embodiments, the device may further comprise a needle access port for collecting a sample. The needle access port may be a luer port. The luer port and/or the needle access point may be angled relative to the housing.

In one or more embodiments, a retractable needle is inserted into the luer port to access a placenta or umbilical cord. The retractable needle may further comprise a reuse prevention element.

In one or more embodiments, the hinging member may be a fixed hinge.

In one or more embodiments, the first sidewall and the second sidewall may be inwardly curved and include a plurality of small protuberances to allow the first sidewall to be secured onto an umbilical cord.

A first and second grasping finger may be disposed on the distal end of the first sidewall and second sidewall, respectively.

In one or more embodiments, the first grasping finger may reciprocally engage the second grasping finger when in a closed position to form a cavity.

In one or more embodiments, the blood collection device may further comprise a syringe having a slidable needle shield inserted into the needle access point to access a placenta or umbilical cord.

In one or more embodiments, the blood collection device may further comprise an integral clamp disposed in the housing to secure an umbilical cord into place or a clamp disposed downstream from the needle access point to prevent blood loss from an umbilical cord.

In one or more embodiments, the blood collection device may further comprise a spring operatively associated with the hinging member for exerting a continual force about the hinging member to urge the first and second sidewalls to a closed position.

In one or more embodiments, the blood collection device may further comprise a needle that is integrally connected to the needle access point. In one or more embodiments, a blood access device or other adapter to enable collection via a blood collection tube may also be connected to the needle access port. In one or more embodiments, the blood access device is a luer lock access device. In one or more embodiments, the needle access point may be adapted to accept a needle with its own integral safety element. In one or more embodiments, the connector port may be a Luer port.

Another aspect of the present invention pertains to a blood collection device comprising a housing to secure an umbilical cord having a first curved sidewall with a first finger hold and a second curved sidewall with a second finger hold; a hinging member for pivotally securing said first sidewall to said second sidewall; an integrated needle; and a needle safety element. The hinging member may be a fixed hinge.

In one or more embodiments, the needle safety element comprises a retractable needle disposed in a chamber integrally connected to the needle access point.

In one or more embodiments, the first sidewall is inwardly curved and includes a plurality of small protuberances to allow the first sidewall to be secured onto an umbilical cord. The second sidewall is also inwardly curved and includes a plurality of small protuberances to allow the second sidewall to be secured onto an umbilical cord.

The device may further comprise a first grasping finger disposed on the distal end of the first sidewall and a second grasping finger disposed on the distal end of the second sidewall. The first grasping finger reciprocally engages the second grasping finger when in a closed position. A cavity may be formed between the first grasping finger and the second grasping finger when in a closed position.

In one or more embodiments, the integrated needle may be disposed at an angle relative to the housing.

The needle safety element may be a slidable needle shield to cover the integrated needle.

In one or more embodiments, the device may further comprise an integral clamp disposed in the housing to secure an umbilical cord into place or a clamp disposed downstream from the integrated needle to prevent blood loss from an umbilical cord.

In one or more embodiments, a spring may be operatively associated with the hinging member for exerting a continual force about said hinging member whereby said first sidewall and second sidewall are urged to a closed position.

In one or more embodiments, a needle housed in a chamber may be integrally connected to a needle access point.

DETAILED DESCRIPTION

Before describing several exemplary embodiments of the invention, it is to be understood that the invention is not limited to the details of construction or process steps set forth in the following description and drawings. The invention is capable of other embodiments and of being practiced or carried out in various ways. Additionally, in the following, items which are substantially the same across the various embodiments are given the same reference numbers.

The present invention provides an improved device for "blood collection" by providing a mechanism to stabilize a placenta or umbilical cord for needle insertion in a safe manner. One or more embodiments of the present invention provide a blood collection device that can be used with one hand such that the placenta or umbilical cord may be stabilized during initial attachment allowing the health care provider to utilize the other hand to maneuver a syringe, forceps or a clamp as needed.

In the present application, the term "needle" is defined to refer to a needle, a cannula or a needle/catheter system to access the blood of an umbilical cord or placenta.

Figure 1:
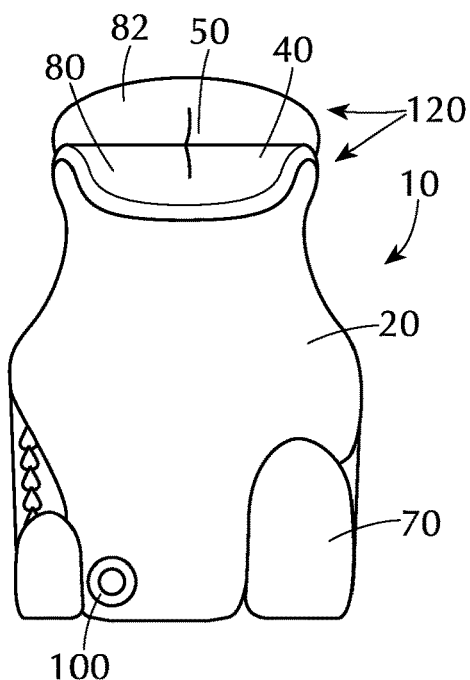
FIG. 1 shows a front view of an embodiment of the placental and cord blood collection device of the present invention.

One or more embodiments of the present invention may have a hinged main body having a set of finger holds. As depicted in FIG. 1, the device 10 comprises a housing to secure a placenta or umbilical cord having a first curved outer sidewall 20 with a first finger hold 80, a second curved sidewall 30 with a second finger hold 82, a hinging member 40 for pivotally securing said first sidewall to said second sidewall, and a needle access point 100 disposed in the housing for needle insertion. The first sidewall 20 and second sidewall 30 define an annular holding chamber 60 in which placenta or umbilical cord is deposited.

In one or more embodiments, the distal end of the first curved outer sidewall 20 and second curved sidewall 30 extends inward to take the form of an inwardly curved grasping/clamping finger 70. At the proximal end of the first curved outer sidewall 20 and second curved sidewall 30, the outer edge of the sidewall takes the form of outwardly curved finger holds 80 and 82. In one or more embodiments, the first curved outer sidewall 20 and second curved sidewall 30 are joined together by a hinging member 40 having a spring 50. Hinging member 40 may be a fixed hinge. The hinge mechanism pivotally couples the first and second sidewalls together at their intermediate portions for pivotal movement between a closed position and an open position. In one or more embodiments, the grasping/clamping fingers 70 also engage each other when the first and second sidewalls pivot to a closed position and the grasping/clamping fingers 70 pivoted apart from each other when the first and second sidewalls pivot to an open position. A cavity is formed between the first grasping finger and the second grasping finger when in a closed position. In one or more embodiments, a wire spring 50 may be used to maintain fingers 70 in "closed" position when not actively opened. In one or more embodiments, the hinging member may be joined and held in a closed position by an alternate force providing member known in the art. Thus, it is contemplated that any driving force element known to one of skill in the art may be used to maintain fingers 70 in "closed" position when not actively opened. Finger holds 80 and 82 open and close fingers 70 to allow the cord to be set in place. Fingers 70 grasp cord for hands free needle insertion. After umbilical cord is grasped, a needle may be inserted into the needle access point 100 for blood collection. In one or more embodiments, a needle safety element, such as a needle shield or sliding sheath or any other needle safety elements which would be obvious to those skilled in the art may cover the needle before and after use. In an embodiment with a fixed needle, needle placement could be made such that insertion could occur as the device was slid upward on the umbilical cord and the needle shield or other safety mechanism simultaneously exposed the needle. In a device with a fixed needle, this could occur through movement of the shield, such as collapsing or withdrawing of the shield. Movement of the shield may be accomplished by other methods known to one of skill in the art. In the case of a mobile needle, the needle may be extended outward into the cord. In one or more embodiments, the device 10 may also include a needle connection port 100 or other adapter to connect syringe or blood bag or other collection container (or tubing to container) to needle/device for blood collection via interior needle. A luer lock access device or other connection to a blood collection vacuum tube may also be used connect to the needle/device for blood collection via interior needle. In one or more embodiments, the needle connection port is a luer port.

Other types of hinging members will be readily apparent to one skilled in the art. An accommodation (not shown) may be positioned at the hinging element 40 for receiving the spring 50. In one or more embodiments, the spring 50 includes two force exertion legs having the same length at both ends thereof. As a result, both finger holds 80 and 82 are subject to the same force in an equilibrium state. The spring 50 may be a conventional torsion spring with a helically coiled body and with two free biasing ends extending from the body. In alternative embodiments, other conventional spring elements, hinging elements or force producing elements can be used as may be desired.

In one or more embodiments, the spring 50 is sufficiently enclosed within a hinging member 40 such that the placenta/umbilical cord does not typically come into contact with and get entangled in the spring.

Figure 2:
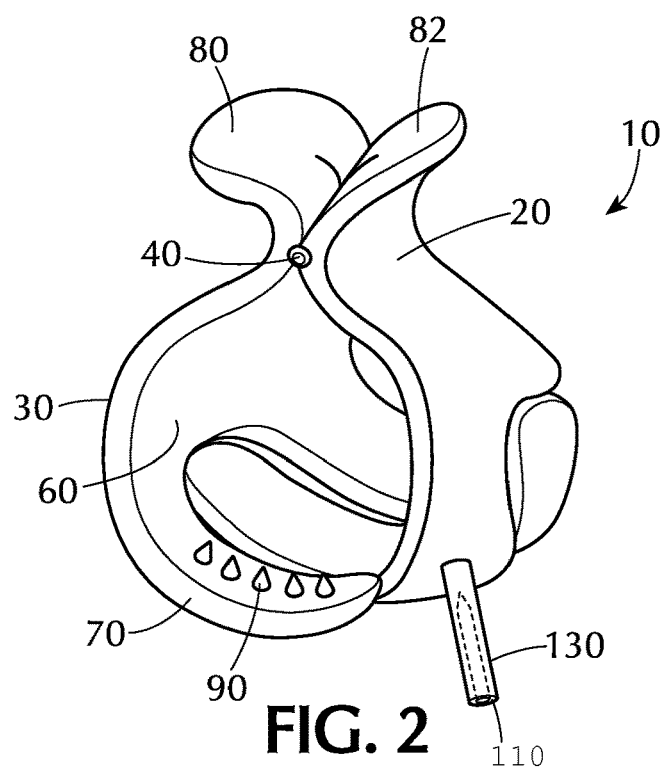
FIG. 2 shows a perspective view of another embodiment of the placental and cord blood collection device of the present invention with needle shield and teeth
Figure 3:
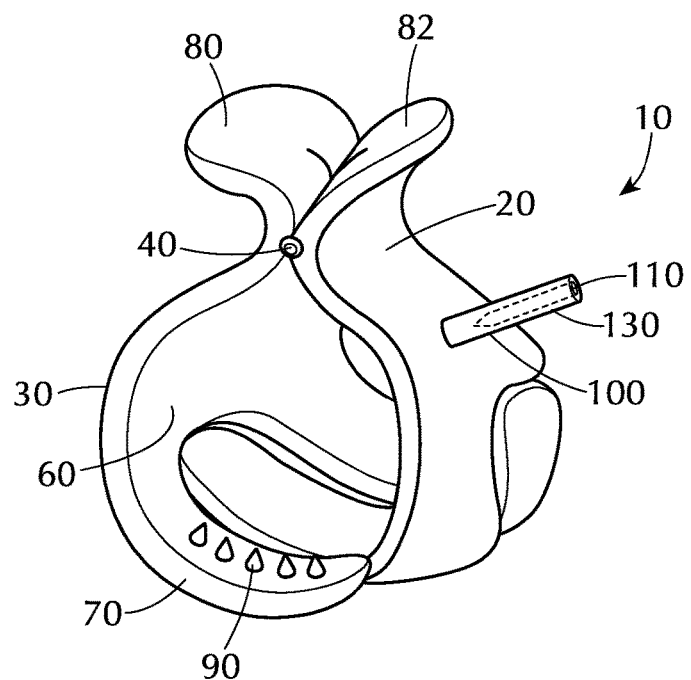
FIG. 3 shows a perspective view of yet another embodiment of the placental and cord blood collection device of the present invention.
Figure 4:
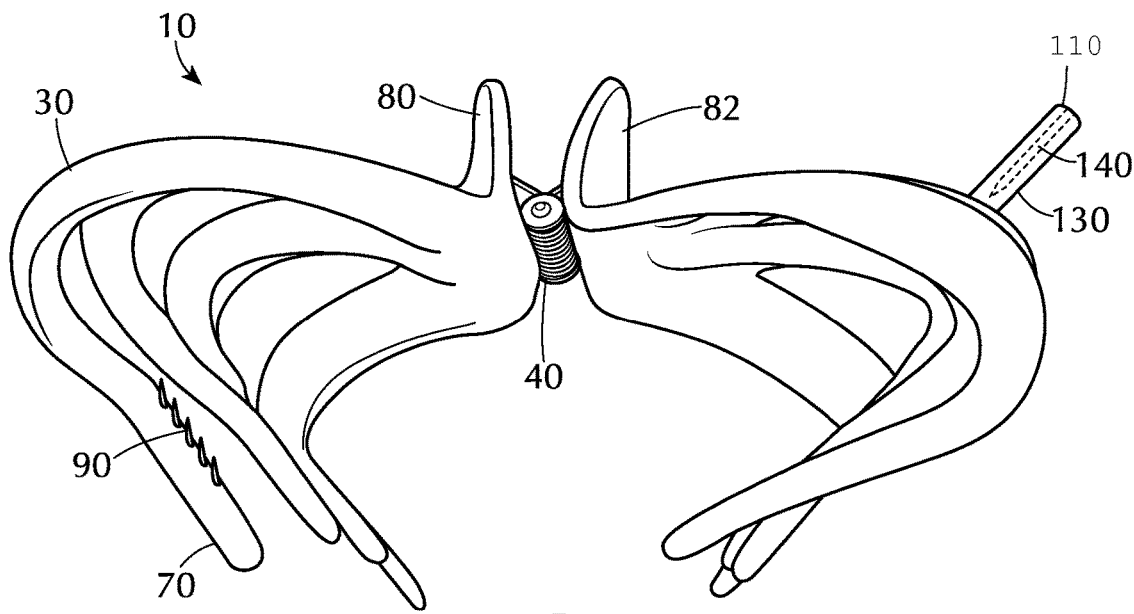
FIG. 4 shows a perspective view of an embodiment of the placental and cord blood collection device of the present invention in an open position as it would receive an umbilical cord.

Pinching or squeezing together of the finger holds 80 and 82 opens the first curved outer sidewall 20 and second curved sidewall 30, as well as, grasping/clamping finger 70 of the device and enables the device 10 to receive a placenta or umbilical cord into annular holding chamber 60. FIG. 4 shows a perspective view of an embodiment of the placental and cord blood collection device of the present invention in an open position. In one or more embodiments, as shown in FIGS. 1-3, the clamping finger 70 has a plurality of small protuberances or teeth 90 which allows the clamping finger 70 to be secured into place during blood collection. The first and second free biasing ends of the spring 50 bias the first and second sidewall toward the closed position.

After releasing pressure on the finger holds 80 and 82 that is required to open the grasping fingers and/or clamping finger 70 of the device, a spring 50 or other force producing element, attached to the hinge 40 would allow the first curved outer sidewall 20 and second curved sidewall 30 to automatically close around the umbilical cord or placenta. In one or more embodiments, spring 50 urges the grasping/clamping fingers 70 of the first and second sidewall to pivot relative to each other towards their closed configuration. Spring 50 can be made of, e.g., stainless steel or plastic that can be deflected under load but that will return to its original shape once the load is released.

In one or more embodiment of the invention, the finger holds 80 and 82 are shorter in length than the grasping fingers &/or clamping fingers 70 so that they remain relatively rigid when the force necessary to open the device is applied to the finger holds 80 and 82.

In one or more embodiment of the invention, as shown in FIG. 2, the distal tips of the first and second sidewalls having a reciprocating grasping/clamping finger 70 configuration. The grasping and/or clamping finger 70 of the first sidewall is curved with its concave side facing towards the opposing grasping and/or clamping finger 70 of the second sidewall. The distal end of first sidewall and second sidewall are formed in an alternating pattern to form grasping and/or clamping fingers 70 that reciprocally engage one another when the grasping/clamping fingers 70 are brought together. Between each grasping/clamping finger 70, there is a cut away section forming a cavity that is positioned relative to the grasping/clamping finger 70 of the opposing sidewall to receive said opposing grasping/clamping finger 70 when the device 10 is in a closed position.

Referring to FIGS. 2 and 3, each finger hold 80 and 82 comprises an upper widened portion. In operation of the blood collection device, when finger holds of the first and second grasping fingers are urged toward each other, the spring flexing about the hinge results in smooth opening action for the clip.

FIGS. 2 and 3 also show a needle shield 130 as one embodiment of a potential safety device to protect the needle 140 or needle cannula before and after use. In addition a luer port 110 allows tubing to a bag or a syringe to be connected to the needle 140. Alternatively, if no needle or needle cannula is present in the device, a a needle access point 100 to allow entry of a needle for piercing tissue through lumen and into the tissue clamped in the recess and the cavity of the clamp jaw. As shown in FIG. 2, a needle access port 110 is included to attach a collection tubing or bag to the needle. As shown in FIG. 3, in one or more embodiments, a syringe having a needle cannula can be inserted into the needle access port 110 to withdraw blood from the placenta or cord. In one or more embodiments, the syringe may include a needle safety element such as a retractable needle that can be retracted before and after use to prevent accidental needle stick injuries to the health care provider or a needle cannula that is shielded with a needle shield. In one or more embodiments, the needle may retract into device 10 after completion of blood collection. In one or more embodiments, a sliding shield element could be used to cover needle after use. It is envisioned that the needle may also be protected by other mechanisms known in the art.

As shown in FIGS. 2 and 3, one or more embodiments of the present invention provide a blood collection device having a grasping finger with a retractable needle for safe cord blood collection. As shown in FIG. 1, the device 10 may have a plurality of projections/teeth 90 to increase the frictional hold of the finger on umbilical cord once the device is set into place. The plurality of projections/teeth 90 may be made of stainless steel or of a flexible material such as silicone, rubber or a thermoplastic elastomer. It is noted that depending on the desired configuration, the plurality of projections/teeth 90 described above, can be mounted on either one or both of the grasping/clamping fingers 70 of the device. In one or more embodiments, the plurality of projections/teeth 90 may be molded or otherwise integrally formed onto the first sidewall or second sidewall.

Furthermore, distal end grasping/clamping finger 70 may be provided with a needle access point 100 to allow entry of a needle for piercing tissue through lumen and into the tissue clamped in the recess and the cavity of the clamp jaw. In one or more embodiments having a interior needle disposed with the device 10, a needle access port 110 is adapted for receipt of a syringe or other collection device to obtain samples from the interior needle.

As shown in FIG. 3, a retractable needle or cannula 140 is mounted to the needle access point in the first or second wall. A needle access port or luer port may be located on the distal end of the chamber 100 to collect blood samples from the needle. In one or more embodiments, the device 10 of the present invention may be provided with a retractable needle that is protected both before and after use to avoid accidental needle sticks. In one or more embodiments, the grasping/clamping fingers 70 are located just below the luer port 100, thus also having the added function of preventing blood from draining lower in the cord before it could be collected. In one or more embodiments, the needle access point is angled relative to the housing so that the needle may be inserted at an angle. In one or more embodiments, the needle access point is a luer port. In one or more embodiments, the luer port is disposed at an angle.

At the onset of a blood collection procedure, a syringe is disposed in a luer port wherein the tip of needle is inserted into vein or artery of the placenta or umbilical cord to allow blood to be withdrawn from the interior of umbilical vein or artery.

Upon the completion of the blood collection procedure, the needle is removed from umbilical cord. A retractable needle may be used to protect against accidental needle sticks both before and after use. In one or more embodiments, a needle retraction feature is incorporated into syringe assemblies to protect users from needle stick injuries. In one or more embodiments, needle hub assembly of the syringe may retracted into the syringe barrel by a retraction feature. The retraction feature may be provided within the syringe barrel and/or the plunger rod disposed within the syringe barrel. In one or more embodiments, the barrel or plunger rod of the syringe may include a chamber that houses the needle after it is retracted. In one or more embodiments, a needle shield or any other needle safety devices known in the art may cover the needle after use.

In another embodiment, as shown in FIG. 3, the needle port is retractable so that the needle is not exposed before cord is secured to eliminate accidental puncture risk. This provides an additional safety feature. In one or more embodiments, the needle and needle port location may be in alternative positions.

Device 10 may include a reuse prevention technology to ensure that the device was only used on one patient. In one or more embodiments, the retractable needle may further comprise a reuse prevention element.

In one or more embodiments, upon retraction, the needle could become locked in place and thereby prevent exposure of the needle a second time after initial use.

In one or more embodiments, additional grasping/clamping fingers 70 may be incorporated to pinch the cord more tightly and secure the device in place. The additional grasping/clamping fingers 70 may also have a plurality of small protuberances or teeth 90 to allow finger 70 to be secured into place during blood collection.

The grasping/clamping fingers 70 could be used to enable more efficient collection of blood, such as those in which the placental tissue is "hung" above the cord to enhance collection with gravity. The grasping/clamping fingers 70 may also be used to massage the placental tissue or perfuse it to increase the collected blood sample.

In one or more embodiments, the grasping portion could be designed to be exposed when the device was pinched open. The needle insertion in this case would not occur by a push button or other mechanism to expose the needle, but instead could be inserted during positioning of the device on the cord.

In one or more embodiments, the blood collection device may further comprise an integral clamp disposed in the housing to secure an umbilical cord into place or a clamp disposed downstream from the needle access point to prevent blood loss from an umbilical cord.

The present invention allows the user to grasp the base of a placenta or umbilical cord with toothed grasping/clamping fingers 70, thus affording the user the ability not to touch the cord or placenta. The device of the present invention allows a user to grasp the cord or placenta with one hand and wipe the cord with a sterile swab with the other hand. The device of the present invention enables a user to steady cord with one hand and attach device and begin collection of cord blood with other hand.

In one or more embodiments of the present invention, the device 10 may have a luer attachment to attach a cord blood bag or syringe or blood access device or Luer lock access device such that a blood collection tube may be connected directly to device to provide a driving force for blood collection. Device 10 may include an upper portion with needle protected by hinged ring 120 during collection and a shield before and after collection. An umbilical cord would be placed into the grasping chamber with the ring in the open position. Needle would be deployed only after the ring was shut to ensure needle safety before and following collection. A lower portion of the sidewall would have grasping/clamping finger 70 including a plurality of small protuberances or teeth 90 which allows blood collection finger 70 to be secured into place during blood collection. The first and second free biasing ends of the spring 50 bias the first and second sidewall toward the closed position. The lower portion of the sidewall also includes luer port 100 to withdraw blood from the placenta or cord. In one or more embodiments, the syringe is a retractable or shielded syringe in which the needle cannula is shielded or retracted before and after use to prevent accidental needle stick injuries to the health care provider. In one or more embodiments, the needle may retract into device 10 after completion of blood collection. In one or more embodiments, a sliding shield element could be used to cover needle after use. It is envisioned that the needle may also be protected by other mechanisms known in the art.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A blood collection device comprising:
   a housing having a first curved sidewall with an outwardly curved first finger hold on a proximal end of the first curved sidewall and a second curved sidewall with a outwardly curved second finger hold on a proximal end of the second curved sidewall, the first curved sidewall and the second curved sidewall defining an annular holding chamber to secure an umbilical cord without cutting or severing the umbilical cord;
   a hinging member pivotally connecting said first sidewall to said second sidewall;
   a needle shield disposed at an angle relative to the housing, a retractable needle mounted inside the needle shield, a luer port at the proximal end of the needle shield;
   a plurality of first grasping fingers disposed on the distal end of the first sidewall, the first sidewall is inwardly curved and the plurality of first grasping fingers having a plurality of small protuberances;
   a plurality of second grasping fingers disposed on the distal end of the second sidewall, the plurality of first grasping fingers orientated in a reciprocating configuration with the plurality of second grasping fingers, the second sidewall is inwardly curved and the plurality of second grasping fingers having a plurality of small protuberances, the plurality of first grasping fingers having a cut away section to receive and reciprocally engage the plurality of second grasping fingers when in a closed position, the plurality of first grasping fingers and plurality of second grasping fingers disposed below the needle shield, the first finger hold being shorter in length than the plurality of first grasping fingers and the second finger hold being shorter in length than the plurality of second grasping fingers;

a cavity formed between the plurality of first grasping fingers and the plurality of second grasping fingers when in a closed position.

2. The blood collection device of claim 1, further comprising a needle access port for collecting a sample.

3. The blood collection device of claim 2 wherein the needle access point is a connector port.

4. The blood collection device of claim 3, wherein the retractable needle is inserted into the connector port to access a placenta or umbilical cord.

5. The blood collection device of claim 4, wherein the retractable needle further comprises a reuse prevention element.

6. The blood collection device of claim 1 wherein the hinging member is a fixed hinge.

7. The blood collection device of claim 3, wherein the connector port is disposed at an angle relative to the housing.

8. The blood collection device of claim 3, further comprising a syringe having a slidable needle shield inserted into the needle access point to access a placenta or umbilical cord.

9. The blood collection device of claim 1 further comprising an integral clamp disposed in the housing to secure an umbilical cord into place.

10. The blood collection device of claim 1 further comprising a clamp disposed downstream from the needle access point to prevent blood loss from an umbilical cord.

11. The blood collection device of claim 1 further comprising a spring operatively associated with said hinging member for exerting a continual force about said hinging member whereby said first sidewall and second sidewall are urged to a closed position.

12. The blood collection device of claim 2, further comprising a blood access device or evacuated tube connected to the needle access point.

13. The blood collection device of claim 2, wherein the needle access point is adapted to accept a needle with its own integral safety element.

14. A blood collection device comprising:
a housing to secure an umbilical cord having a first inwardly curved sidewall with a first outwardly curved finger hold on a proximal end of the first curved sidewall and a second inwardly curved sidewall with a second outwardly curved finger hold on a proximal end of the second curved sidewall, the first curved sidewall and the second curved sidewall defining an annular holding chamber to secure an umbilical cord without cutting or severing the umbilical cord;
a hinging member for pivotally securing said first sidewall to said second sidewall;
an retractable needle disposed inside a needle shield, the needle shield being integrally connected to a needle access port to access the contents of the needle, the needle shield being disposed at an angle relative to the housing;
a spring operatively associated with said hinging member for exerting a continual force about said hinging member whereby said first sidewall and second sidewall are urged to a closed position, the spring enclosed within the hinging member such that the umbilical cord does not contact the spring;
a plurality of first grasping fingers disposed on the distal end of the first sidewall, the plurality of first grasping fingers having a plurality of small protuberances;
a plurality of second grasping fingers disposed on the distal end of the second sidewall, the plurality of second grasping fingers having a plurality of small protuberances, the plurality of first grasping fingers orientated in a reciprocating configuration with the plurality of second grasping fingers, the plurality of first grasping fingers reciprocally engage the plurality of second grasping fingers when in a closed position; and
a cavity formed between the first grasping finger and the second grasping finger when in a closed position.

15. The blood collection device of claim 14 wherein the hinging member is a fixed hinge.

16. The blood collection device of claim 14 further comprising an integral clamp disposed in the housing to secure an umbilical cord into place.

17. The blood collection device of claim 14 further comprising a clamp disposed downstream from the integrated needle to prevent blood loss from an umbilical cord.

18. The blood collection device of claim 14, further comprising a blood access device or evacuated tube connected to the needle via a needle access point.

* * * * *